United States Patent
Maddur et al.

(10) Patent No.: US 11,744,584 B2
(45) Date of Patent: Sep. 5, 2023

(54) ALIGNMENT PIN ASSEMBLY FOR SURGICAL STAPLER

(71) Applicant: Covidien LP, Mansfield, MA (US)

(72) Inventors: Jeevan Shankar Setty Maddur, Bangalore (IN); Anant Tiwari, Hyderabad (IN)

(*) Notice: Subject to any disclaimer, the term of this patent is extended or adjusted under 35 U.S.C. 154(b) by 178 days.

(21) Appl. No.: 17/328,313

(22) Filed: May 24, 2021

(65) Prior Publication Data

US 2021/0378668 A1    Dec. 9, 2021

Related U.S. Application Data

(60) Provisional application No. 63/036,693, filed on Jun. 9, 2020.

(51) Int. Cl.
*A61B 17/072* (2006.01)
*A61B 17/068* (2006.01)

(52) U.S. Cl.
CPC ........ *A61B 17/072* (2013.01); *A61B 17/0686* (2013.01); *A61B 2017/07221* (2013.01); *A61B 2017/07228* (2013.01); *A61B 2017/07257* (2013.01); *A61B 2017/07271* (2013.01); *A61B 2017/07285* (2013.01)

(58) Field of Classification Search
CPC ........ A61B 17/072; A61B 2017/07221; A61B 2017/07228; A61B 2017/07285; A61B 2017/07257
USPC ....................................................... 227/180.1
See application file for complete search history.

(56) References Cited

U.S. PATENT DOCUMENTS

| | | | |
|---|---|---|---|
| 1,158,111 | A | 10/1915 | Ahlheim |
| 2,891,250 | A | 6/1959 | Hirata |
| 3,080,564 | A | 3/1963 | Strekopitov et al. |
| 3,252,643 | A | 5/1966 | Strekopov et al. |
| 3,269,630 | A | 8/1966 | Fleischer |
| 3,275,211 | A | 9/1966 | Hirsch et al. |
| 3,315,863 | A | 4/1967 | O'Dea |

(Continued)

OTHER PUBLICATIONS

Diameter Definition & Meaning—Merriam-Webster. URL https://www.merriam-webster.com/dictionary/diameter (Year: 2023).*

(Continued)

*Primary Examiner* — Valentin Neacsu
(74) *Attorney, Agent, or Firm* — Carter, DeLuca & Farrell LLP (57) ABSTRACT

A surgical stapling instrument includes an elongate body portion defining a longitudinal axis, an end effector supported on a distal portion of the elongated body portion, and a deployment member extending from the elongate body portion into the end effector. The end effector includes a housing having a base portion and a jaw portion, an anvil assembly supported on the jaw portion, and a cartridge assembly releasably supported on the base portion. The cartridge assembly includes an alignment pin assembly. The deployment member includes a distal portion supporting an abutment member and is movable between a retracted position and an advanced position. The abutment member is releasably coupled to the alignment pin assembly when the deployment member is in the retracted position and is fixedly secured to the alignment pin assembly when the deployment member is moved from the retracted position.

17 Claims, 9 Drawing Sheets

(56) References Cited

U.S. PATENT DOCUMENTS

| | | | |
|---|---|---|---|
| 3,494,533 A * | 2/1970 | Green | A61B 17/072 227/19 |
| 3,589,589 A | 6/1971 | Akopov | |
| 3,692,224 A | 9/1972 | Astafiev et al. | |
| 3,795,034 A | 3/1974 | Strekopytov et al. | |
| 3,822,818 A | 7/1974 | Strekopytov et al. | |
| 3,935,981 A | 2/1976 | Akopov et al. | |
| 3,949,923 A | 4/1976 | Akopov et al. | |
| 4,047,654 A | 9/1977 | Alvarado | |
| 4,216,891 A | 8/1980 | Behlke | |
| 4,244,372 A | 1/1981 | Kapitanov et al. | |
| 4,296,881 A | 10/1981 | Lee | |
| 4,305,539 A | 12/1981 | Korolkov et al. | |
| 4,354,628 A * | 10/1982 | Green | A61B 17/072 227/19 |
| 4,378,901 A | 4/1983 | Akopov et al. | |
| 4,383,634 A * | 5/1983 | Green | A61B 17/072 227/135 |
| 4,402,444 A | 9/1983 | Green | |
| 4,415,112 A | 11/1983 | Green | |
| D273,513 S | 4/1984 | Spreckelmeier | |
| 4,442,964 A | 4/1984 | Becht | |
| 4,470,533 A | 9/1984 | Schuler | |
| 4,475,679 A | 10/1984 | Fleury, Jr. | |
| 4,485,811 A | 12/1984 | Chernousov et al. | |
| 4,506,670 A | 3/1985 | Crossley | |
| 4,506,671 A | 3/1985 | Green | |
| 4,508,253 A * | 4/1985 | Green | A61B 17/072 227/135 |
| 4,522,327 A | 6/1985 | Korthoff et al. | |
| 4,527,724 A | 7/1985 | Chow et al. | |
| 4,530,453 A | 7/1985 | Green | |
| 4,550,870 A | 11/1985 | Krumme et al. | |
| 4,566,620 A | 1/1986 | Green et al. | |
| 4,568,009 A | 2/1986 | Green | |
| 4,573,622 A | 3/1986 | Green et al. | |
| 4,580,712 A * | 4/1986 | Green | A61B 17/072 227/19 |
| 4,585,153 A | 4/1986 | Failla et al. | |
| 4,589,582 A | 5/1986 | Bilotti | |
| 4,602,634 A | 7/1986 | Barkley | |
| 4,605,001 A | 8/1986 | Rothfuss et al. | |
| 4,605,004 A | 8/1986 | Di Giovanni et al. | |
| 4,606,344 A | 8/1986 | Di Giovanni | |
| 4,606,345 A | 8/1986 | Dorband et al. | |
| 4,607,636 A | 8/1986 | Kula et al. | |
| 4,612,933 A | 9/1986 | Brinkerhoff et al. | |
| 4,617,928 A | 10/1986 | Alfranca | |
| 4,632,290 A | 12/1986 | Green et al. | |
| 4,665,916 A | 5/1987 | Green | |
| 4,684,051 A | 8/1987 | Akopov et al. | |
| 4,714,187 A | 12/1987 | Green | |
| 4,715,520 A | 12/1987 | Roehr, Jr. et al. | |
| 4,728,020 A | 3/1988 | Green et al. | |
| 4,767,044 A | 8/1988 | Green | |
| 4,788,978 A | 12/1988 | Strekopytov et al. | |
| 4,802,614 A | 2/1989 | Green et al. | |
| 4,805,823 A | 2/1989 | Rothfuss | |
| 4,819,853 A | 4/1989 | Green | |
| 4,848,637 A | 7/1989 | Pruitt | |
| 4,869,414 A | 9/1989 | Green et al. | |
| 4,881,544 A | 11/1989 | Green et al. | |
| 4,881,545 A | 11/1989 | Isaacs et al. | |
| 4,915,100 A | 4/1990 | Green | |
| 4,930,503 A | 6/1990 | Pruitt | |
| 4,938,408 A | 7/1990 | Bedi et al. | |
| 4,941,623 A | 7/1990 | Pruitt | |
| 4,951,861 A | 8/1990 | Schulze et al. | |
| 4,964,559 A | 10/1990 | Deniega et al. | |
| 5,005,754 A | 4/1991 | Van Overloop | |
| 5,018,657 A | 5/1991 | Pedlick et al. | |
| 5,071,052 A | 12/1991 | Rodak et al. | |
| 5,100,042 A | 3/1992 | Gravener et al. | |
| 5,116,349 A | 5/1992 | Aranyi | |
| 5,137,198 A | 8/1992 | Nobis et al. | |
| 5,172,845 A | 12/1992 | Tejeiro | |
| 5,190,203 A | 3/1993 | Rodak | |
| 5,219,111 A | 6/1993 | Bilotti et al. | |
| 5,240,163 A | 8/1993 | Stein et al. | |
| 5,344,060 A | 9/1994 | Gravener et al. | |
| 5,368,599 A | 11/1994 | Hirsch et al. | |
| 5,405,073 A | 4/1995 | Porter | |
| 5,413,267 A | 5/1995 | Solyntjes et al. | |
| 5,439,155 A | 8/1995 | Viola | |
| 5,452,836 A | 9/1995 | Huitema et al. | |
| 5,458,279 A | 10/1995 | Plyley | |
| 5,462,215 A | 10/1995 | Viola et al. | |
| 5,464,144 A | 11/1995 | Guy et al. | |
| 5,465,894 A | 11/1995 | Clark et al. | |
| 5,470,006 A | 11/1995 | Rodak | |
| 5,470,008 A | 11/1995 | Rodak | |
| 5,470,009 A | 11/1995 | Rodak | |
| 5,497,934 A | 3/1996 | Brady et al. | |
| 5,503,320 A | 4/1996 | Webster et al. | |
| 5,509,596 A | 4/1996 | Green et al. | |
| 5,542,594 A | 8/1996 | McKean et al. | |
| 5,547,117 A | 8/1996 | Hamblin et al. | |
| 5,558,266 A * | 9/1996 | Green | A61B 17/072 227/19 |
| 5,579,978 A | 12/1996 | Green et al. | |
| 5,580,067 A | 12/1996 | Hamblin et al. | |
| 5,603,443 A | 2/1997 | Clark et al. | |
| 5,605,272 A | 2/1997 | Witt et al. | |
| 5,605,273 A | 2/1997 | Hamblin et al. | |
| 5,607,094 A | 3/1997 | Clark et al. | |
| 5,615,820 A | 4/1997 | Viola | |
| 5,641,111 A | 6/1997 | Ahrens et al. | |
| 5,678,748 A | 10/1997 | Plyley et al. | |
| 5,697,543 A | 12/1997 | Burdorff | |
| 5,706,997 A | 1/1998 | Green et al. | |
| 5,706,998 A | 1/1998 | Plyley et al. | |
| 5,732,871 A | 3/1998 | Clark et al. | |
| 5,735,445 A | 4/1998 | Vidal et al. | |
| 5,794,834 A | 8/1998 | Hamblin et al. | |
| 5,810,240 A | 9/1998 | Robertson | |
| 5,855,311 A | 1/1999 | Hamblin et al. | |
| 5,878,937 A | 3/1999 | Green et al. | |
| 5,893,506 A | 4/1999 | Powell | |
| 5,894,979 A | 4/1999 | Powell | |
| 5,964,394 A | 10/1999 | Robertson | |
| 6,045,560 A | 4/2000 | McKean et al. | |
| 6,638,285 B2 | 10/2003 | Gabbay | |
| 6,805,273 B2 | 10/2004 | Bilotti et al. | |
| 6,817,508 B1 | 11/2004 | Racenet et al. | |
| 6,988,650 B2 | 1/2006 | Schwemberger et al. | |
| 7,070,083 B2 | 7/2006 | Jankowski | |
| 7,134,587 B2 | 11/2006 | Schwemberger et al. | |
| 7,147,139 B2 | 12/2006 | Schwemberger et al. | |
| 7,147,140 B2 | 12/2006 | Wukusick et al. | |
| 7,204,404 B2 | 4/2007 | Nguyen et al. | |
| 7,207,472 B2 | 4/2007 | Wukusick et al. | |
| 7,210,609 B2 | 5/2007 | Leiboff et al. | |
| 7,237,708 B1 | 7/2007 | Guy et al. | |
| 7,275,674 B2 | 10/2007 | Racenet et al. | |
| RE40,237 E | 4/2008 | Bilotti et al. | |
| 7,407,076 B2 | 8/2008 | Racenet et al. | |
| 7,431,190 B2 | 10/2008 | Hoffman | |
| 7,522,854 B2 | 4/2009 | Kinouchi et al. | |
| 7,549,563 B2 | 6/2009 | Mather et al. | |
| 7,568,605 B2 | 8/2009 | Kruszynski | |
| 7,641,092 B2 | 1/2010 | Kruszynski et al. | |
| 7,717,312 B2 | 5/2010 | Beetel | |
| 7,731,073 B2 | 6/2010 | Wixey et al. | |
| 7,735,704 B2 | 6/2010 | Bilotti | |
| 7,766,207 B2 | 8/2010 | Mather et al. | |
| 7,810,690 B2 | 10/2010 | Bilotti et al. | |
| 7,886,953 B2 | 2/2011 | Schwemberger et al. | |
| 8,016,176 B2 | 9/2011 | Kasvikis et al. | |
| 8,029,520 B2 | 10/2011 | Korvick et al. | |
| 8,033,439 B2 | 10/2011 | Racenet et al. | |
| 8,070,038 B2 | 12/2011 | Kostrzewski | |
| 8,231,041 B2 | 7/2012 | Marczyk et al. | |
| 8,292,904 B2 | 10/2012 | Popovic et al. | |

(56) References Cited

U.S. PATENT DOCUMENTS

| | | |
|---|---|---|
| 8,360,296 B2 | 1/2013 | Zingman |
| 8,424,738 B2 | 4/2013 | Kasvikis |
| 8,499,994 B2 | 8/2013 | D'Arcangelo |
| 8,596,515 B2 | 12/2013 | Okoniewski |
| 8,627,994 B2 | 1/2014 | Zemlok et al. |
| 8,646,673 B2 | 2/2014 | Bilotti et al. |
| 8,757,467 B2 | 6/2014 | Racenet et al. |
| 8,936,185 B2 | 1/2015 | Racenet et al. |
| 8,955,732 B2 | 2/2015 | Zemlok et al. |
| 8,967,446 B2 | 3/2015 | Beardsley et al. |
| 9,022,273 B1 | 5/2015 | Marczyk et al. |
| 9,125,651 B2 | 9/2015 | Mandakolathur Vasudevan et al. |
| 9,192,382 B2 | 11/2015 | Kostrzewski |
| 9,814,460 B2 | 11/2017 | Kimsey et al. |
| 9,888,923 B2 | 2/2018 | Chen et al. |
| 10,194,913 B2 | 2/2019 | Nalagatla et al. |
| 2004/0164123 A1 | 8/2004 | Racenet et al. |
| 2005/0247752 A1 | 11/2005 | Kelly et al. |
| 2005/0247753 A1 | 11/2005 | Kelly et al. |
| 2006/0163312 A1 | 7/2006 | Viola et al. |
| 2007/0187456 A1 | 8/2007 | Viola et al. |
| 2010/0048988 A1 | 2/2010 | Pastorelli et al. |
| 2010/0282820 A1* | 11/2010 | Kasvikis .............. A61B 17/068 227/181.1 |
| 2011/0233261 A1* | 9/2011 | Rao ...................... A61B 17/068 227/175.1 |
| 2013/0206813 A1 | 8/2013 | Nalagatla |
| 2016/0249914 A1 | 9/2016 | Zhang et al. |
| 2017/0014134 A1 | 1/2017 | Chen et al. |
| 2017/0027571 A1 | 2/2017 | Nalagatla et al. |
| 2017/0027572 A1 | 2/2017 | Nalagatla et al. |
| 2017/0027573 A1 | 2/2017 | Nalagatla et al. |
| 2017/0027574 A1 | 2/2017 | Nalagatla et al. |
| 2017/0189022 A1 | 7/2017 | Adams et al. |
| 2017/0340324 A1 | 11/2017 | Gong et al. |
| 2018/0049739 A1* | 2/2018 | Kasvikis .............. A61B 17/072 |
| 2019/0239886 A1* | 8/2019 | Jones .................. A61B 17/2841 |

OTHER PUBLICATIONS

Integral Definition & Meaning—Merriam-Webster. URL https://www.merriam-webster.com/dictionary/integral (Year: 2023).*
Snap Definition & Meaning—Merriam-Webster. URL https://www.merriam-webster.com/dictionary/snap (Year: 2023).*
European Search Report dated Feb. 7, 2022, corresponding to counterpart European Application No. 21175798.4; 11 pages.

* cited by examiner

ALIGNMENT PIN ASSEMBLY FOR SURGICAL STAPLER

CROSS-REFERENCE TO RELATED APPLICATION

This application claims the benefit of and priority to U.S. Provisional Application No. 63/036,693, filed on Jun. 9, 2020, the entire contents of which being incorporated by reference herein.

FIELD

The present disclosure relates generally to a surgical stapling instrument including a replaceable cartridge assembly having an alignment pin and, more specifically, to a surgical stapling instrument including a replaceable cartridge assembly having an alignment pin that is selectively securable to a deployment member of the surgical stapling instrument.

BACKGROUND

Surgical stapling instruments used for applying parallel rows of staples through compressed living tissue are well known in the art, and are commonly used, for example, for closure of tissue or organs during surgical procedures for performing anastomoses and/tissue transection or resection. Surgical stapling instruments are often used for occlusion of organs in thoracic and abdominal procedures. Typically, surgical stapling instruments include an anvil assembly, a cartridge assembly for supporting an array of surgical staples, an approximation mechanism for approximating the anvil and cartridge assemblies, and a firing mechanism for ejecting the surgical staples from the cartridge assembly.

The cartridge assembly may include an alignment pin for capturing tissue between the cartridge and anvil assemblies and for maintaining alignment between the cartridge and anvil assemblies during approximation and firing of the surgical stapling instrument. Typically, the surgical instrument includes a deployment assembly that can be manually operated to advance the alignment pin from within the cartridge assembly into engagement with the anvil assembly. Alternatively, the deployment assembly may be automatically actuated upon operation of the approximation mechanism to advance the alignment pin.

To facilitate reuse of these surgical stapling instruments, the cartridge assemblies may be configured for removal following use, thereby permitting replacement of the cartridge of the surgical stapling instrument. A need exists for a surgical stapling instrument which includes an alignment pin that remains secure to the deployment assembly of the surgical stapling instrument during a surgical stapling procedure and to permit release of the alignment pin from the deployment assembly following the stapling procedure.

SUMMARY

A surgical stapling instrument including a replaceable cartridge assembly is provided. The surgical stapling instrument includes an elongate body portion defining a longitudinal axis, an end effector supported on a distal portion of the elongated body portion, and a deployment member extending from the elongate body portion into the end effector. The end effector includes a housing having a base portion and a jaw portion, an anvil assembly supported on the jaw portion, and a cartridge assembly releasably supported on the base portion. The cartridge assembly includes an alignment pin assembly. The deployment member includes a distal portion supporting an abutment member. The deployment member is movable between a retracted position and an advanced position. The abutment member is releasably coupled to the alignment pin assembly when the deployment member is in the retracted position, and is fixedly secured to the alignment pin assembly when the deployment member is moved from the retracted position.

In aspects of the disclosure, the alignment pin assembly includes a base member having an engagement portion. The engagement portion may be engageable with the abutment member of the deployment member. The housing of the cartridge assembly may define a recess. The engagement portion of the base member may be aligned with the recess in the housing when the deployment member is in the retracted position. The engagement portion of the base member may be out of alignment with the recess in the housing when the deployment member is moved from the retracted position. The engagement portion may be configured to be cantilevered into the recess in the housing when the deployment member is in the retracted position. The engagement portion may include a snap feature configured to engage the abutment member of the deployment member to maintain engagement between the base member and the deployment member.

In other aspects of the disclosure, the alignment pin assembly includes a base member and an alignment pin extending from the base member. The base member may include a pair of wings and the housing of the cartridge assembly may define a pair of slots. The wings may be received within the slots to prevent rotation of the base member. The housing may include an alignment pin retaining portion defining a channel for receiving the alignment pin assembly.

Also provided is a replaceable cartridge assembly. The replaceable cartridge assembly includes a housing supporting a plurality of staples. The housing includes a base portion and an alignment pin retaining portion. The alignment pin retaining portion defines a channel and a recess. The replaceable cartridge assembly also includes an alignment pin assembly slidably disposed within the channel and moveable between a retracted position and an advanced position. The alignment pin assembly includes a base member and an alignment pin extending from the base member. The base member includes an engagement portion that is movable from a first position to a second position within the recess to facilitate coupling of the engagement portion with a deployment member of a surgical stapling instrument. The engagement portion is aligned with the recess when the alignment pin assembly is in the retracted position to permit the engagement portion to move into the second position within the recess.

In certain aspects of the disclosure, the engagement portion of the base member includes a snap feature and the deployment member includes an abutment member. The snap feature may be configured to maintain engagement between the base member and the deployment member. The base member may include a pair of wings and the housing may define a pair of slots. The wings may be received within the slots to prevent rotation of the base member. The housing may be configured to be releasably secured to an end effector of a surgical stapling instrument. The base member and the alignment pin may be integrally formed. The engagement portion may be out of alignment with the recess when the alignment pin assembly is moved from the retracted position. The housing may be curved.

BRIEF DESCRIPTION OF THE DRAWINGS

Aspects of the disclosed surgical stapling instrument are described herein with reference to the drawings, wherein.

DETAILED DESCRIPTION OF THE DRAWINGS

Aspects of the disclosed replaceable cartridge assembly for surgical stapling instruments are described in detail with reference to the drawings, wherein like reference numerals designate corresponding elements in each of the several views. In the drawings and the description that follow, the term "proximal" refers to the end of the surgical stapling instrument that is closer to the clinician, whereas the term "distal" refers to the end of the surgical stapling instrument that is farther from the clinician. In addition, the term "clinician" is used generally to refer to medical personnel including doctors, nurses, and support personnel.

It should be appreciated that the instruments described and illustrated herein are configured to fire surgical staples against an anvil surface; however, aspects of the present disclosure are equally applicable with other forms of staples, fasteners, clips, as well as two-part fasteners, made of metallic and/or polymeric materials.

Embodiments of the presently disclosed surgical stapling instruments include a curved end effector having a curved anvil assembly and a curved cartridge assembly. It is envisioned that the aspects of the present disclosure may be suitable for use with surgical stapling instruments having linear end effectors.

Figure 1:
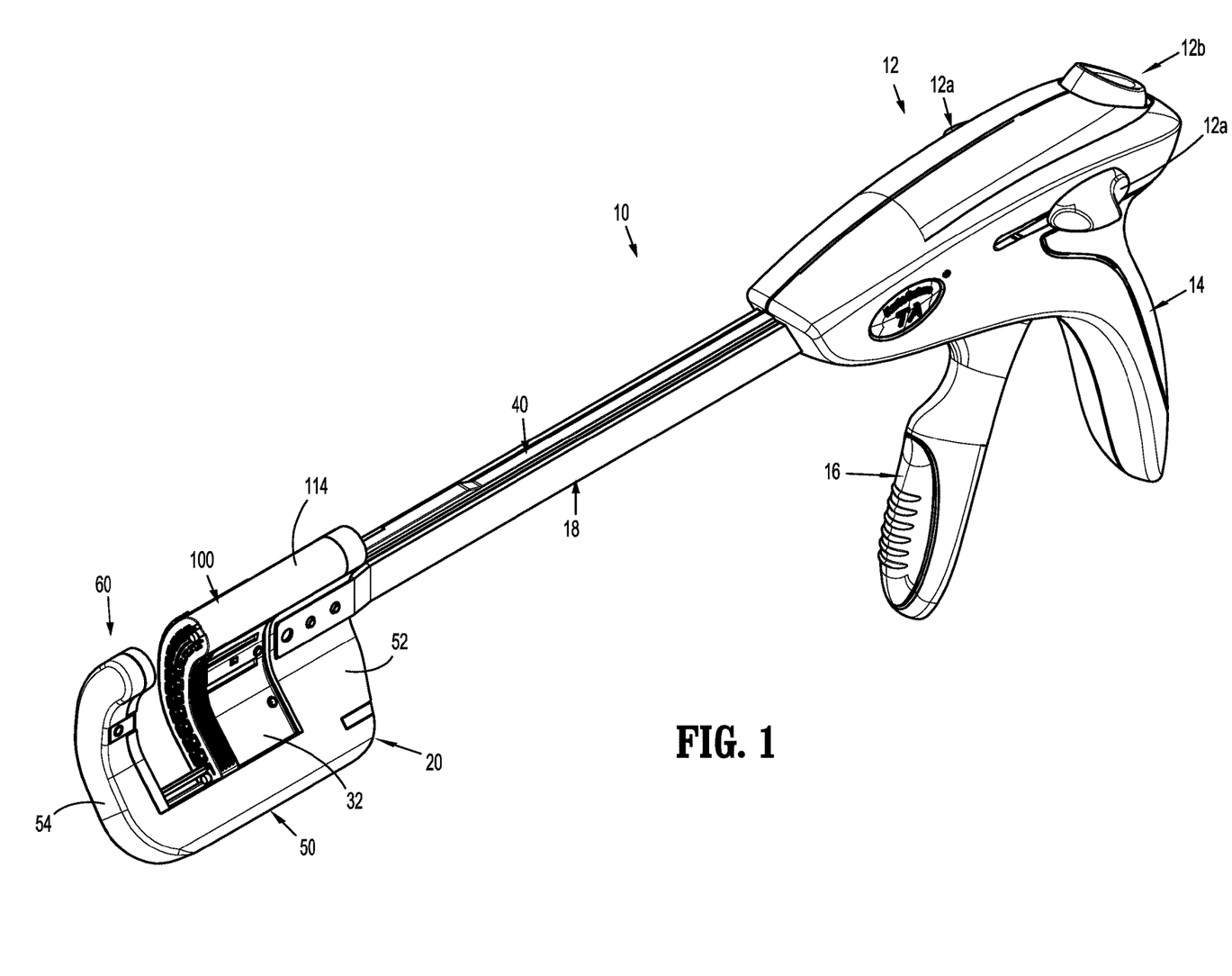
FIG. 1 is a side perspective view of a surgical stapling instrument according to exemplary aspects of the disclosure including an end effector supporting a replaceable cartridge assembly with the end effector in an open position.

With initial reference to FIG. 1, an exemplary embodiment of the presently disclosed surgical stapling instrument including a replaceable cartridge assembly 100 is shown generally as stapling instrument 10. The stapling instrument 10 includes a body 12 defining a stationary handle 14, a pivotable trigger 16 movable relative to the stationary handle 14, an elongated central body portion 18 extending from the body 12, and an end effector 20 disposed on a distal end of the elongated central body portion 18. The end effector 20 of the stapling instrument 10 includes an anvil assembly 60 and a replaceable cartridge assembly 100.

A thumb button 12a is slidably positioned on each side of the body 12 of the stapling instrument 10. The thumb buttons 12a are movable to manually advance an alignment pin 154 (FIG. 4) of an alignment pin assembly 150 (FIG. 4) of the replaceable cartridge assembly 100. A release button 12b is positioned on the proximal end of body 12 of the stapling instrument 10 and is depressible to allow the replaceable cartridge assembly 100 to return from an approximated position (not shown) disposed adjacent to the anvil assembly 60 (FIG. 1) to an open position spaced from the anvil assembly 60.

The stapling instrument 10 will be described to the extent necessary to fully disclose the aspects of the present disclosure. For a detailed description of the internal structure and function of an exemplary surgical stapling instrument, please refer to commonly owned U.S. Pat. No. 6,817,508 ("the '508 patent"), and commonly owned U.S. patent application Ser. No. 15/826,837 ("the '837 application), filed Nov. 30, 2017, the contents of which are incorporated by reference herein in their entireties. Although described with reference to the stapling instrument 10, it is envisioned that the aspects of present disclosure may be modified for use with any instrument having an alignment pin.

Figure 2:
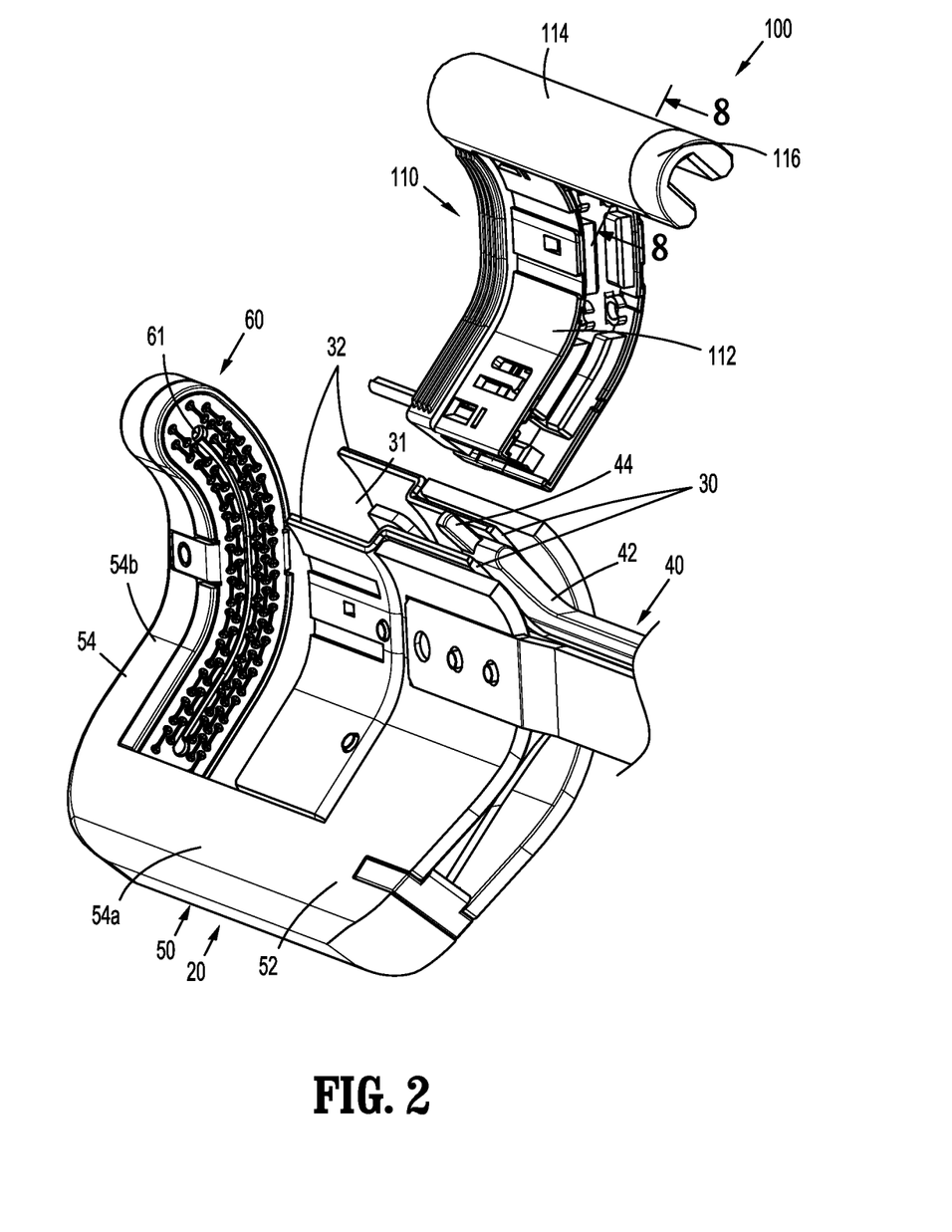
FIG. 2 is a perspective view of the end effector of the surgical stapling instrument shown in FIG. 1 with the replaceable cartridge assembly removed from the end effector.

With reference to FIG. 2, the end effector 20 of the stapling instrument 10 (FIG. 1) includes a frame 50 having a base portion 52 and an L-shaped jaw portion 54 extending from the base portion 52. The L-shaped portion 54 includes a longitudinal portion 54a and a transverse portion 54b. The anvil assembly 60 is supported on the transverse portion 54b of the jaw portion 54 of the frame assembly 50 and the cartridge assembly 100 is releasably supported within a head portion 32 of clamp slide members 30 within the base portion 52 of the frame assembly 50.

The base portion 52 and the transverse portion 54b of the jaw portion 54 of the frame assembly 50 of the end effector 20 are curved. In embodiments, the base portion 52 and the transverse portion 54b of the jaw portion 54 of the frame assembly 50 of the end effector 20 are substantially C-shaped although other curved and linear configurations are also envisioned. In embodiments, the end effector 20 includes a first radius of curvature and a second radius of curvature. The first and second radii of curvature may be increased or decreased to suit a particular procedure and/or to facilitate access to a particular body cavity or location within a body cavity. In some embodiments, the end effector 20 is formed by a plurality of substantially linear sections that are connected to each other to define a curved-like configuration. Each of the anvil assembly 60 and the cartridge assembly 100 include a curved configuration corresponding to the curved configuration of the frame assembly 50 of the end effector 20.

With continued reference to FIG. 2, the head portions 32 of the clamp slide members 30 of stapling instrument 10 support the replaceable cartridge assembly 100 and are slidably supported within the base portion 52 of the frame assembly 50 of the end effector 20. As disclosed in the '837 application, the clamp slide members 30 advance in response to actuation of the trigger 16 (FIG. 1) of the stapling instrument 10 (FIG. 1) to cause advancement of the replaceable cartridge assembly 100 relative to the anvil assembly 60. The head portions 32 of the clamp slide members 30 define a channel 31 configured to releasably support the replaceable cartridge assembly 100. For a detailed description of the structure and operation of an exemplary end effector, please refer to the '837 application.

Figure 3:
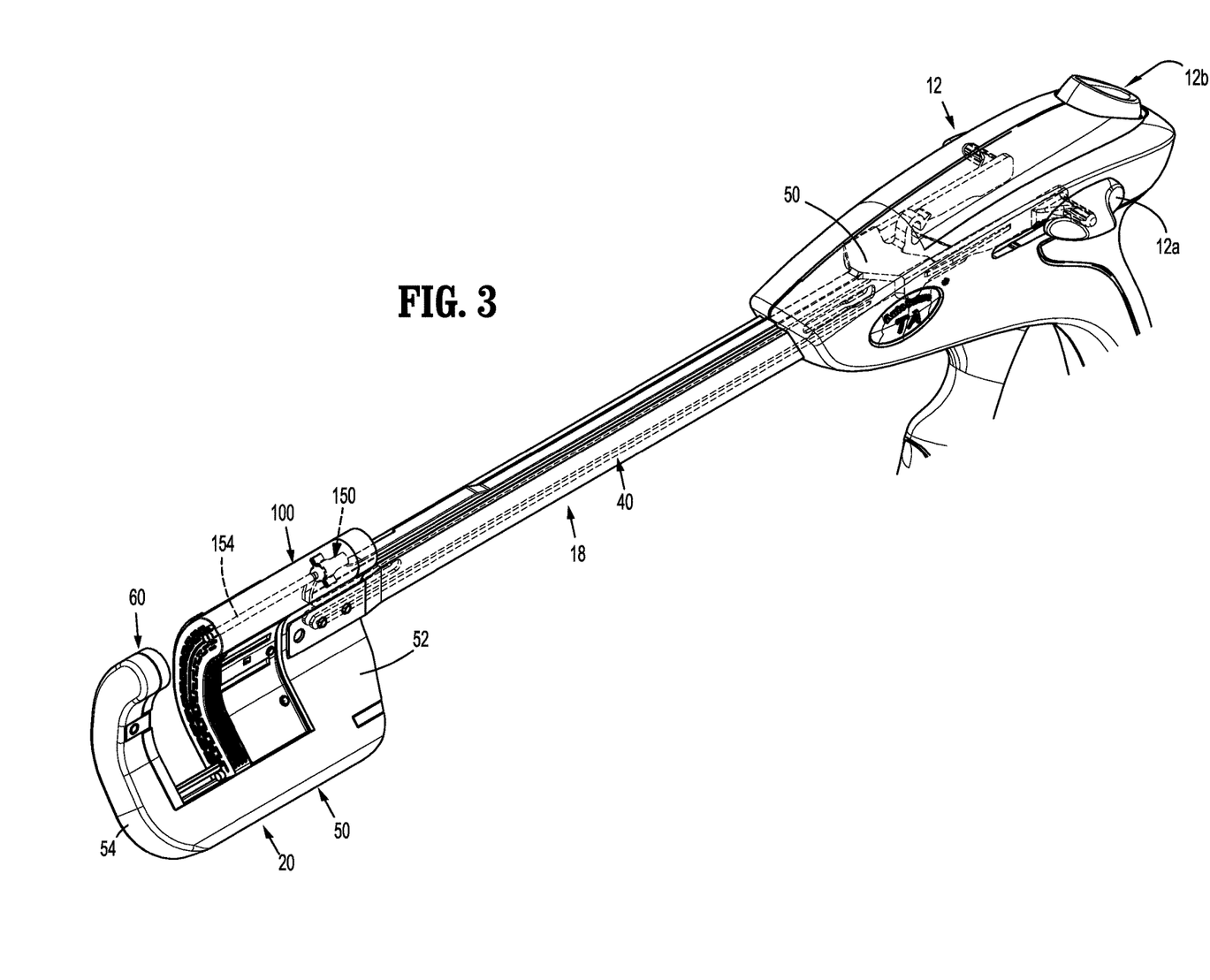
FIG. 3 is a side perspective view of the surgical stapling instrument shown in FIG. 1 with a deployment member and an alignment pin assembly shown in phantom.

With additional reference to FIG. 3, the stapling instrument 10 includes an alignment pin pusher or deployment member 40 that is slidably supported within the elongated central body portion 18 of the stapling instrument 10. The deployment member 40 has a distal end including an abutment member 44 that is positioned to engage with the alignment pin 154 of the alignment pin assembly 150 of the cartridge assembly 100 when the cartridge assembly 100 is supported on the end effector 20. The deployment member 40 is operable to advance and retract the alignment pin 154 of the alignment pin assembly 150. More specifically, the deployment member 40 is movable in response to movement of trigger 16 during an approximation stroke of the stapling instrument 10 to advance the alignment pin 154 of the alignment pin assembly 150 from a position within the cartridge assembly 100 into engagement with the anvil assembly 60. Alternatively, the deployment member 40 can be manually advanced using the thumb buttons 12a. The deployment member 40 will only be described to the extent necessary to fully disclose the aspects of the present disclosure. For a detailed description of an exemplary deployment member, please refer to the '508 patent, the content of which is incorporated herein by reference in its entirety.

The deployment member 40 of the stapling instrument 10 includes a vertical portion 42 (FIG. 2) that supports the abutment member 44 (FIG. 2). The abutment member 44 is configured to engage the alignment pin 154 of the alignment pin assembly 150 of the replaceable cartridge assembly 100 such that when the deployment member 40 is advanced, the alignment pin 154 is advanced from within cartridge 100 into an opening 61 (FIG. 2) of the anvil assembly 60.

Figures 4, 5:
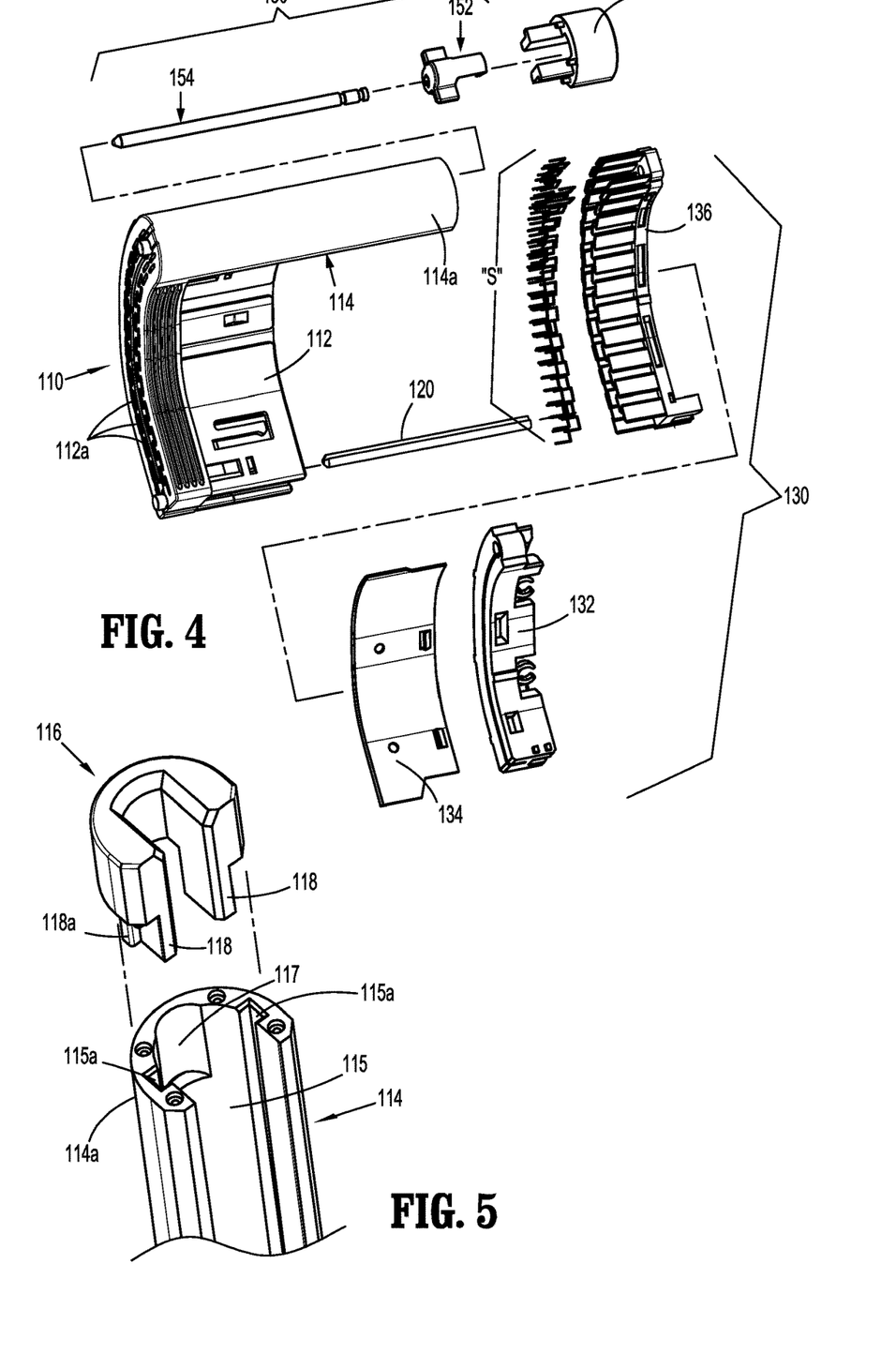
FIG. 4 is a side perspective view of the replaceable cartridge assembly shown in FIG. 2 with parts separated.
FIG. 5 is a perspective view of a pin retaining portion of a housing and an end cap of the replaceable cartridge assembly shown in FIG. 4 with parts separated.

With reference now to FIG. 4, the replaceable cartridge assembly 100 of the stapling instrument 10 includes a housing 110, a pusher assembly 130, and the alignment pin assembly 150. The cartridge assembly 100 will only be described to the extent necessary to fully disclose the aspects of the present disclosure. For a detailed description of the structure and operation of an exemplary pusher assembly, please refer to the '837 application.

The housing 110 of the cartridge assembly 100 includes a base portion 112 that defines a plurality of staple receiving pockets 112a that support a plurality of staples "S". The base portion 112 defines a channel (not shown) that is configured to receive the pusher assembly 130 to eject the staples "S" from the base portion 112. The housing 110 also includes an alignment pin retaining portion 114 that is configured to receive the alignment pin assembly 150. As will be described in further detail below, the alignment pin assembly 150 is maintained within the alignment pin retaining portion 114 by an end cap 116. The base portion 112 also supports a tissue guide 120.

The pusher assembly 130 of the cartridge assembly 100 includes a knife pusher 132, a knife 134 extending from the knife pusher 132, and a staple pusher 136 that is operably engageable with the knife pusher 132. During actuation of the stapling instrument 10, the knife pusher 132, the knife 134, and the staple pusher 136 are advanced to staple and cut tissue (not shown) received between the anvil assembly 60 and the cartridge assembly 100.

With additional reference to FIG. 5, the alignment pin retaining portion 114 of the housing 110 of the replaceable cartridge assembly 100 defines a longitudinal channel 115 for receiving the alignment pin assembly 150. The alignment pin retaining portion 114 of the housing 110 further defines a pair of slots 115a extending along the longitudinal channel 115 that provides an anti-rotation feature for the alignment pin assembly 150. A proximal portion 114a of the alignment pin retaining portion 114 of the housing 110 defines a recess or relief 117. As will be describe in detail below, the recess 117 permits releasable engagement between the alignment pin assembly 150 and the deployment member 40 (FIG. 3).

With particular reference to FIG. 5, the end cap 116 of the cartridge assembly 100 engages the proximal portion 114a of the alignment pin retaining portion 114 of the housing 110. As shown, the end cap 116 includes a pair of extensions 118, and a flange 118a extending from each of the extensions 118. The extensions 118 of the end cap 116 are received within the longitudinal channel 115 in the alignment pin retaining portion 114 of the housing 110 and the flanges 118a are received within the slots 115a in the alignment pin retaining portion 114 of the housing 110 to attach the end cap 116 to alignment pin retaining portion 114. The end cap 116 may be secured to the alignment pin retaining portion 114 of the housing 110 with friction fit, adhesive, welding, mechanical fasteners, or in any other suitable manner.

Figure 6:
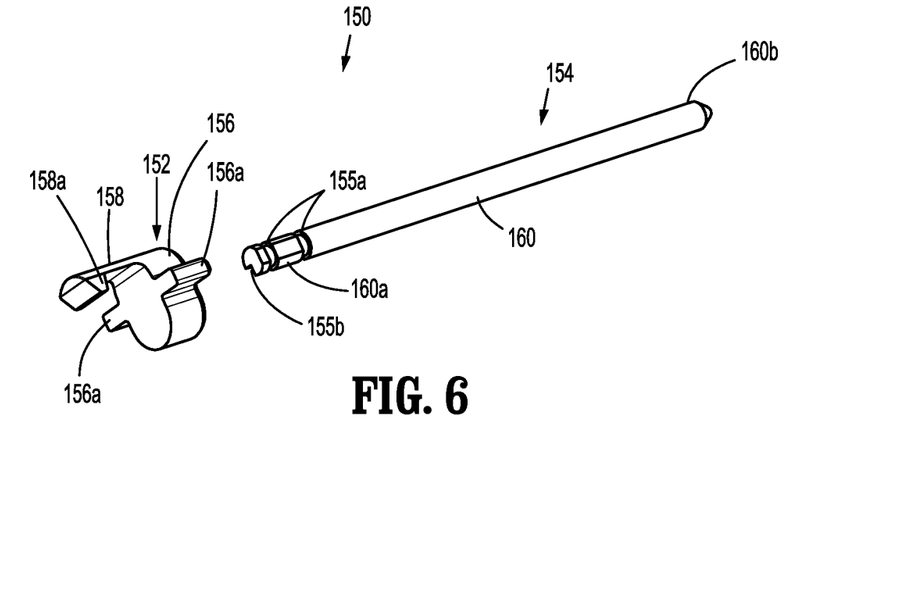
FIG. 6 is a perspective side view of the alignment pin assembly of the replaceable cartridge assembly shown in FIG. 4 with parts separated.
Figure 7:
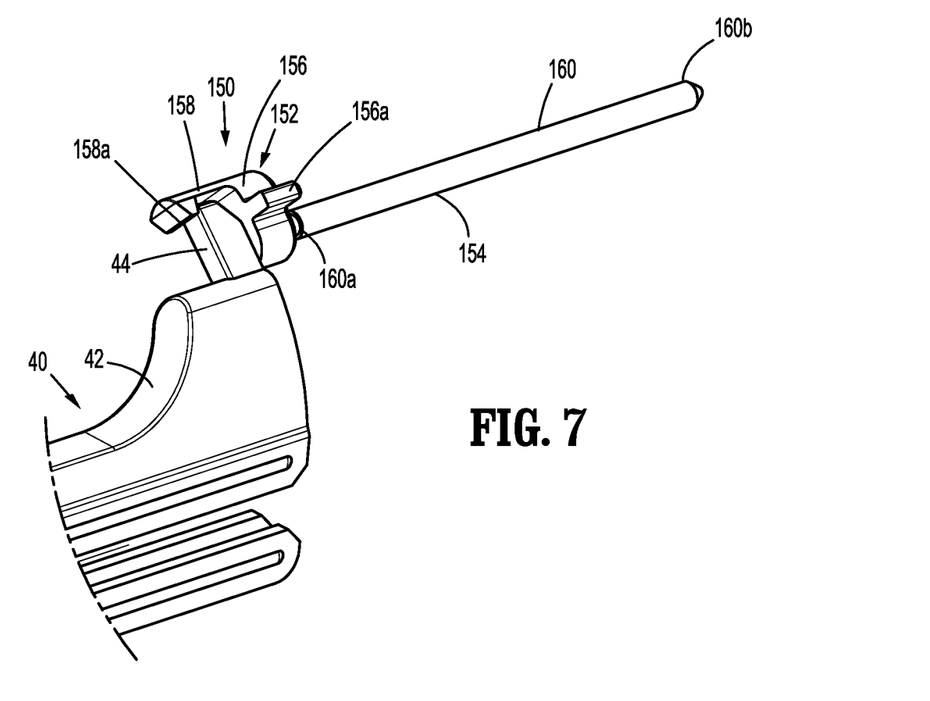
FIG. 7 is a perspective view of the alignment pin assembly shown in FIG. 6, assembled and secured to the deployment member of the surgical stapling instrument shown in FIG. 3.
Figure 8:
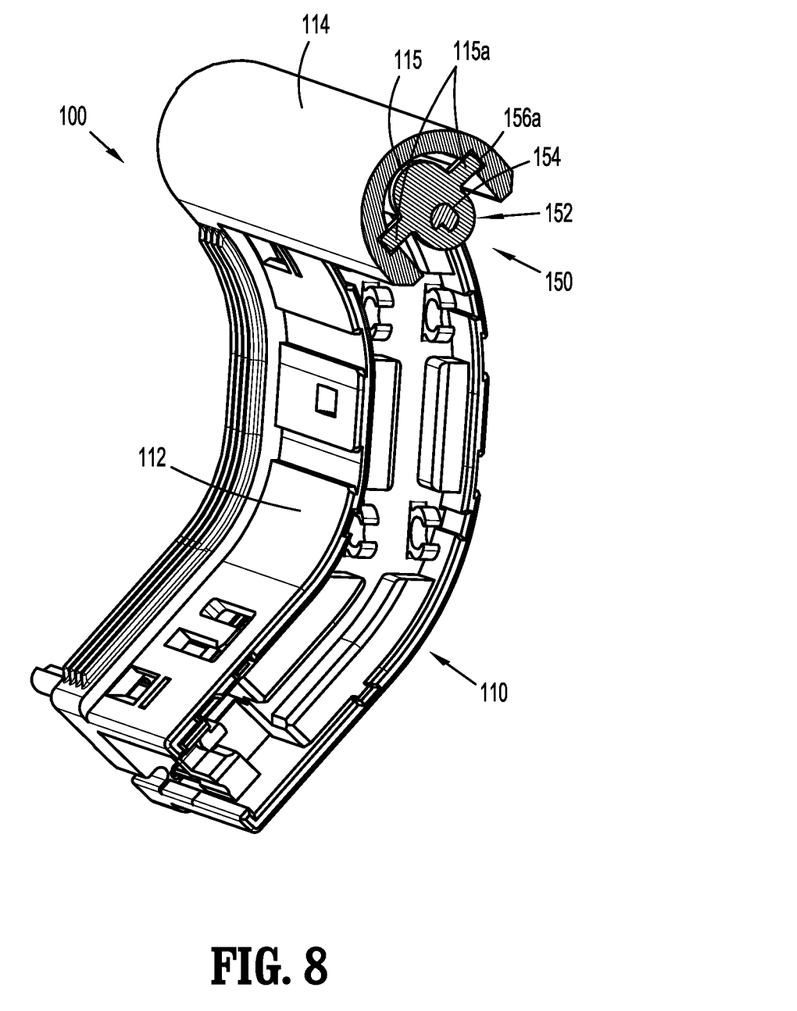
FIG. 8 is a cross-sectional view taken along section line 8-8 of FIG. 2.

With reference now to FIGS. 6 and 7, the alignment pin assembly 150 includes a base member 152 and the alignment pin 154. The alignment pin 154 extends from the base member 152 distally towards the anvil assembly 60 when the cartridge assembly 100 is secured to the clamp slide members 30 (FIG. 2.) Although shown as being separate components, it is envisioned that the base member 152 and the alignment pin 154 may be integrally formed with each other. The base member 152 of the pin assembly 150 includes a body portion 156 and a pair of wings 156a extending outwardly from the body portion 156. The body portion 156 is slidably receivable within the longitudinal channel 115 in the alignment pin retaining portion 114 of the housing 110 and the wings 156a are receivable within the slots 115a in the alignment pin retaining portion 114 of the housing 110. Receipt of the wings 156a of the base member 152 within the slots 115a of the alignment pin retaining portion 114 prevent rotation of the alignment pin assembly 150 within the longitudinal channel 115 during operation of the stapling instrument 10 (FIG. 1).

Figure 12:
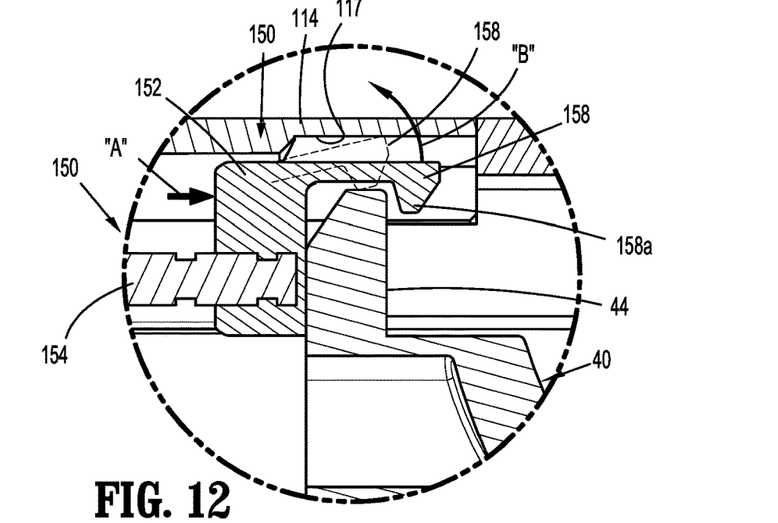
FIG. 12 is an enlarged view of the indicated area of detail shown in FIG. 11.

The base member 152 of the alignment pin assembly 150 includes an engagement portion 158 extending proximally from the body portion 156 of the base member 152. The engagement portion 158 includes a snap feature 158a disposed on a proximal end of the engagement portion 158. The snap feature 158a is configured to engage the abutment member 44 (FIG. 7) of the deployment member 40 of the stapling instrument 10 when the cartridge assembly 100 is secured to the end effector 20 of the stapling instrument 10. The engagement portion 158 of the base member 152 of the alignment pin assembly 150 is configured to cantilever or deflect into the recess 117 formed in the alignment pin retaining portion 114 of the housing 110 of the cartridge assembly 100, as shown in FIG. 12, to permit engagement and disengagement of the snap feature 158a of the engagement portion 158 of the alignment pin assembly 150 with the abutment member 44 of the deployment member 40, thereby forming a snap-fit connection. The location of the recess 117 in the alignment pin retaining portion 114 of the housing 110 is such that the engagement portion 158 of the base member 152 may only be received within the recess 117 to facilitate coupling of the engagement portion 158 and the abutment member 44 when the alignment pin is 154 is in a retracted position (FIG. 10), i.e., prior to advancement of the alignment pin 154.

The alignment pin 154 of the alignment pin assembly 150 includes an elongate body 160 having a proximal portion 160a configured for engagement with the base member 152 of the alignment pin assembly 150 and tapered distal portion 160b configured to facilitate receipt within an opening 61 (FIG. 2) formed in the anvil assembly 60 (FIG. 2). The proximal portion 160a of the alignment pin 154 may include one or more grooves 155a, one or more notches 155b, or be otherwise configured for secure engagement with the base member 152. The proximal portion 160a of the alignment pin 154 may be secured to the base member 152 with friction fit, adhesive, welding, or in any other suitable manner.

Figures 9, 10:
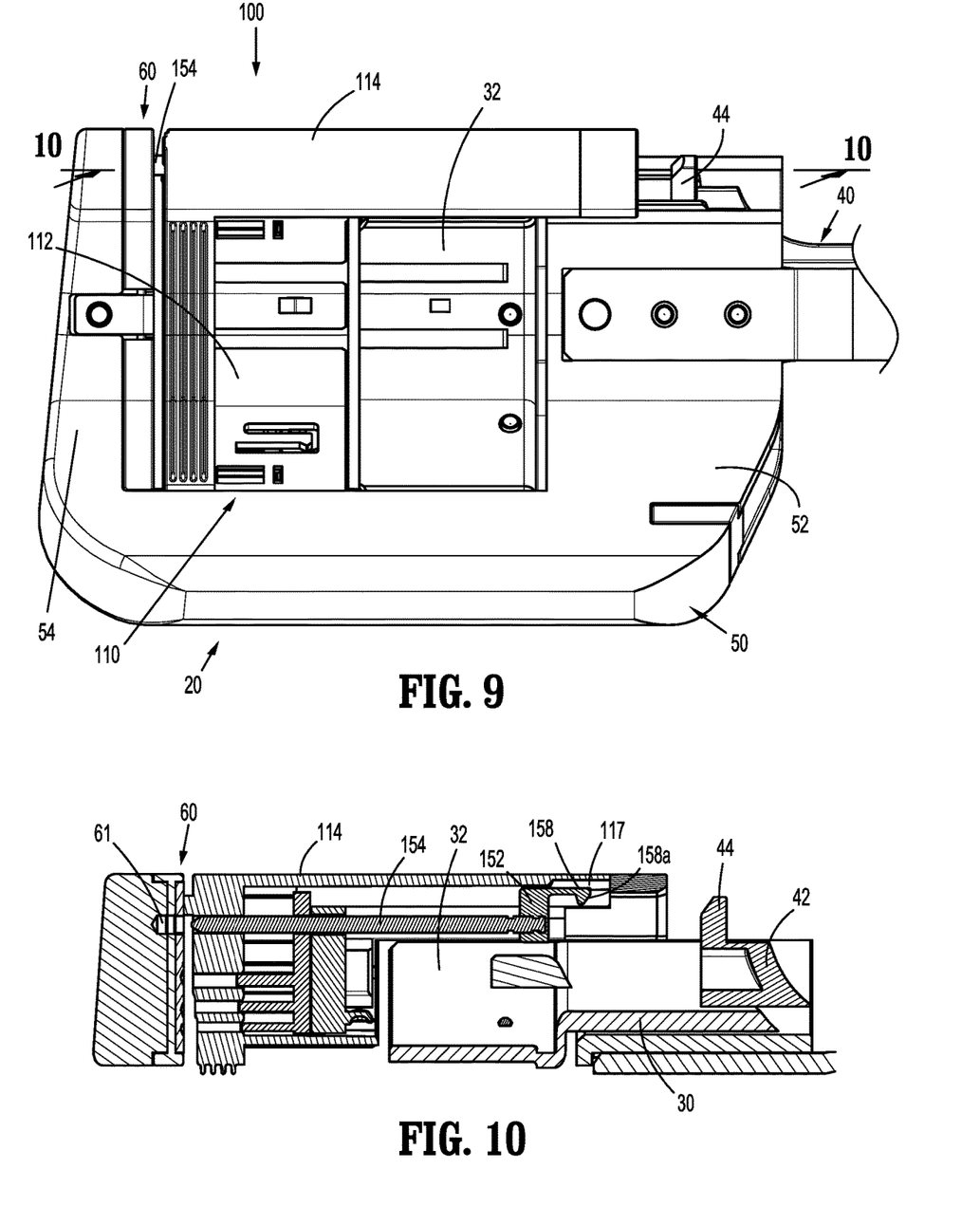
FIG. 9 is a side view of the end effector of the surgical stapling instrument shown in FIG. 1 with the replaceable cartridge assembly partially loaded onto the end effector.
FIG. 10 is a cross-sectional side view taken along section line 10-10 of FIG. 9.

The operation of the replaceable cartridge assembly 100 will now be described with reference to FIGS. 2 and 9-13. Referring briefly to FIG. 2, to load the cartridge 100 assembly 100 onto the end effector 20, the cartridge assembly 100 is initially slid downwardly between the head portions 32 of the clamp slide members 30 to the position shown in FIGS. 9 and 10 to a partially loaded position. Thereafter, the cartridge assembly 100 is slid proximally in the direction indicated by arrow "A" in FIG. 11 to a fully loaded position. Referring initially to FIGS. 9 and 10, in the partially loaded position, the alignment pin assembly 150 of the replaceable cartridge assembly 100 is shown in a first or retracted position. In the retracted position, the engagement portion 158 of the base member 152 of the alignment pin assembly 150 is aligned with the recess 117 in the alignment pin retaining portion 114 of the housing 110 of the replaceable cartridge assembly 100, as shown in FIG. 10.

The replaceable cartridge assembly 100 is moved from the position shown in FIG. 2 to the partially loaded position of FIGS. 9 and 10 with the alignment pin 154 in the retracted position by first receiving the base portion 112 of the housing 110 between the anvil assembly 60 and the head portions 32 of the clamp slide members 30 (FIG. 2) of the stapling instrument 10. More particularly, the body portion 112 of the housing 110 of the replaceable cartridge assembly 100 is aligned with the channel 31 (FIG. 2) defined by the head portions 32 of the clamp slide members 30.

Figure 11:
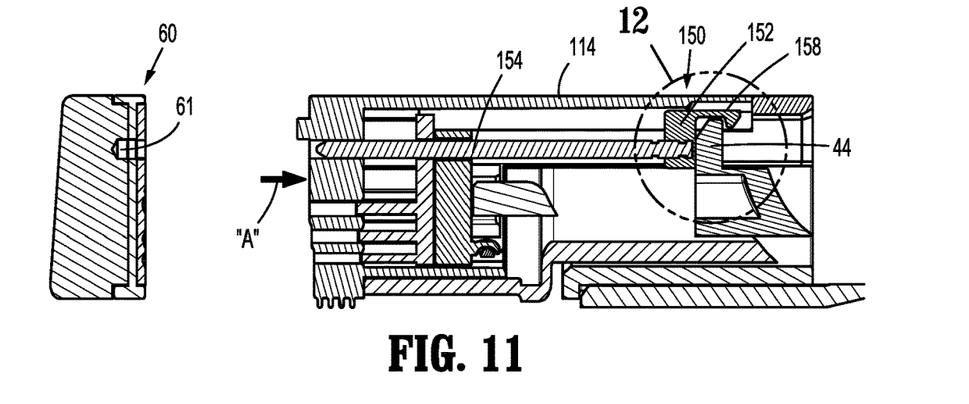
FIG. 11 is a cross-sectional side view of the end effector taken along section line 10-10 of FIG. 9 with the cartridge assembly in a fully loaded position.

The cartridge assembly 100 is moved from the partially loaded position shown in FIGS. 9 and 10 to the fully loaded position shown in FIGS. 11 and 12 by moving the replaceable cartridge assembly 100 in a proximal direction relative to the frame assembly 50, as indicated by arrow "A", such that the replaceable cartridge assembly 100 is received within the channel 31 between the head portions 32 of the clamp slide members 30. As the replaceable cartridge assembly 100 is moved in the proximal direction, the snap feature 158a on the engagement portion 158 of the base member 152 of the alignment pin assembly 150 engages the abutment member 44 of the deployment member 40 to cause the engagement portion 158 of the base member 152 to cantilever in an upward direction, as indicated by arrow "B" in FIG. 12, into recess 117 formed in the alignment pin retaining portion 114 of the housing 110 of the replaceable cartridge assembly 100. Either or both of the engagement portion 158 and the abutment member 44 may have an angled surface, as shown, to facilitate the cantilevered movement of the engagement portion 158 and to allow the abutment member 44 to move distally past the engagement portion 158.

Figure 13:
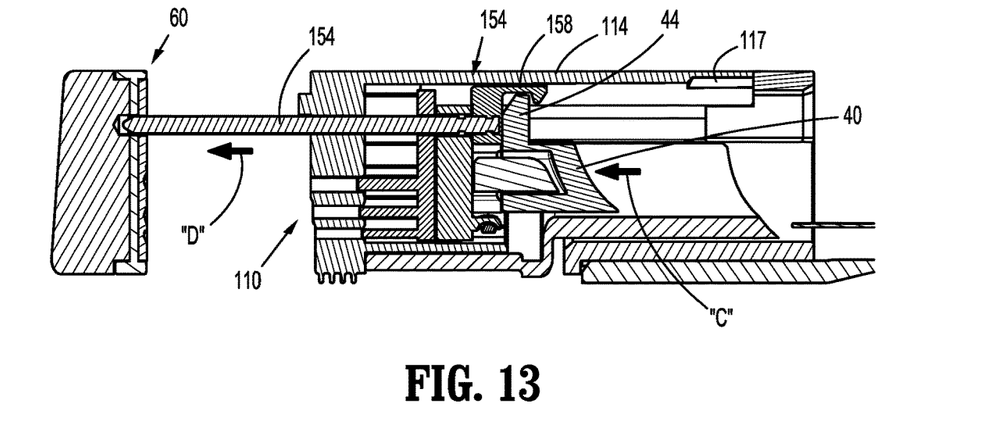
FIG. 13 is a cross-sectional side view taken along section line 10-10 shown in FIG. 9, with the end effector in an open position and the alignment pin assembly in an advanced position.

Continued proximal movement of the replaceable cartridge assembly 100 permits the engagement portion 158 of the base member 152 of the alignment pin assembly 150 to return to the pre-cantilevered position, as shown in FIG. 13, to secure the base member 152 to the deployment member 40. More particularly, the snap feature 158a extending from the engagement portion 158 of the base member 152 of the alignment pin assembly 150 engages the abutment member 44 of the deployment member 40 to secure the alignment pin 154 to the deployment member 40.

Turning to FIG. 13, advancement of the deployment member 40 in the distal direction, as indicated by arrow "C", causes the alignment pin assembly 150 to advance, i.e., move in the distal direction, as indicated by arrow "D". As noted above, the deployment member 40 may be advanced, as shown, prior to approximation of the replaceable cartridge assembly 100 through use of the thumb buttons 12a (FIG. 1) of the stapling instrument 10, or during actuation of the stapling instrument 10 (FIG. 1). As the alignment pin assembly 150 is advanced, the base member 152 of the alignment pin assembly 150 is moved out of alignment with the recess 117 in the alignment pin retaining portion 114 of the housing 110 of the replaceable cartridge assembly 100. In this manner, the engagement portion 158 of the base member 152 is unable to cantilever out of engagement with the abutment member 44 of the deployment member 40, thereby maintaining the engagement between the base member 152 and the deployment member 40.

Figure 14:
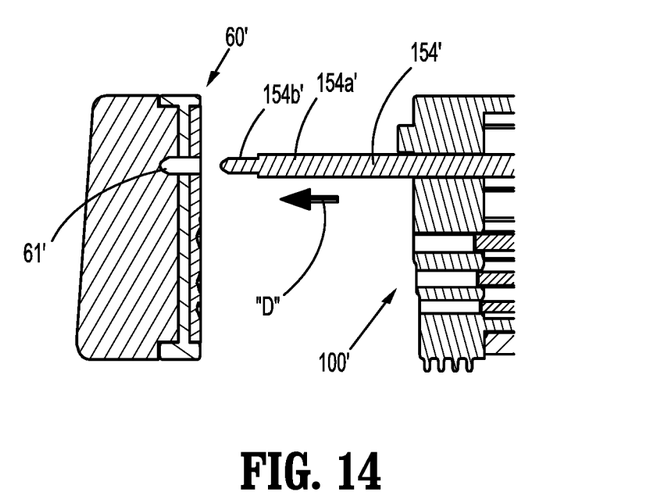
FIG. 14 is a cross-sectional side view of an end effector including a cartridge assembly according to another aspect of the disclosure in a fully loaded position and an alignment pin of the cartridge assembly in a partially advanced position.
Figure 15:
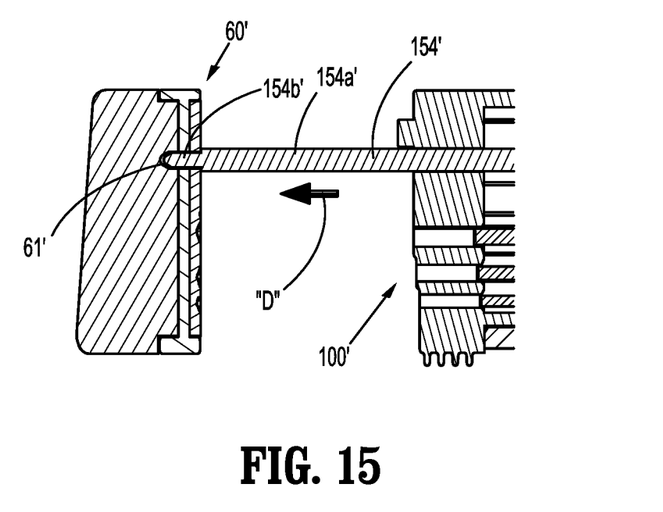
FIG. 15 is the cross-sectional side view shown in FIG. 14, with the end effector in an open position and the alignment pin in an advanced position.

Turning briefly to FIGS. 14 and 15, another aspect of the disclosure is shown with regards to a replaceable cartridge assembly 100'. The replaceable cartridge assembly 100' includes a stepped alignment pin 154' having a proximal portion 154a' with a first diameter, and a distal portion 154b' with a second diameter, the second diameter being smaller than the first diameter. The larger diameter proximal portion 154a' of the stepped alignment pin 154' provides increased strength and less alignment warpage of the stepped alignment pin 154' during use. The smaller diameter distal portion 154b' of the stepped alignment pin 154' requires less space, i.e., a smaller opening 61' in anvil assembly 60'.

Following the actuation of the end effector 20, the alignment pin assembly 150 is retracted to an initial position within the replaceable cartridge assembly 100 through retraction of the deployment member 40 of the stapling instrument 10. The return of the alignment pin assembly 150 to the retracted position realigns the engagement portion 158 of the base member 152 of the alignment pin assembly 150 with the recess 117 in the alignment pin retaining portion 114 of the housing 110 of the replaceable cartridge assembly 100. As such, when the cartridge assembly 100 is moved distally in relation to the clamp slide members 30 to disconnect the cartridge assembly 100 from the clamp slide members 30 and the abutment member 44 engages the engagement portion 158 of the base member 152, the engagement portion 158 may cantilever or deflect into the recess 117 in the alignment pin retaining portion 114 of the housing 110. This facilitates separation of the alignment pin assembly 150 from the deployment member 40 of the stapling instrument 10, and removal of the replaceable cartridge assembly 100 from the end effector 20.

The stapling instrument 10 may then be reused during the same procedure by loading the end effector 20 with one or more unused or fresh cartridge assemblies 100. Alternatively, the stapling instrument 10 may be cleansed and sterilized for use in one or more subsequent procedures.

It will be understood that various modifications may be made to the embodiments disclosed herein. For example, the components of the surgical stapling instrument can be formed of any material suitable for surgical use and having the required strength characteristics. Therefore, the above description should not be construed as limiting, but merely as exemplifications of preferred embodiments. Those skilled in the art will envision other modifications within the scope and spirit of the claims appended hereto.

What is claimed is:

1. A surgical stapling instrument comprising:
   an elongate body portion defining a longitudinal axis;
   an end effector supported on a distal portion of the elongated body portion, the end effector including:
   a housing having a base portion and a jaw portion, the base portion being secured to the distal portion of the elongate body portion;
   an anvil assembly supported on the jaw portion; and
   a cartridge assembly releasably supported on the base portion, the cartridge assembly including a housing and an alignment pin assembly, the housing including an alignment pin retaining portion that receives the alignment pin assembly to facilitate movement of the alignment pin assembly within the housing between a pin retracted position and a pin advanced position, the alignment pin retaining portion having an inner wall defining a recess, the alignment pin assembly including a base member having an engagement portion that is movable into the recess from a first position to a second position when the alignment pin assembly is in the pin retracted position; and
   a deployment member extending from the elongate body portion into the end effector and including a distal portion supporting an abutment member, the abutment member engaged with the engagement portion of the base member of the alignment pin assembly, the deployment member being movable between a retracted position and an advanced position to move the alignment pin assembly between the pin retracted position and the pin advanced position, wherein the inner wall of the alignment pin retaining portion prevents movement of the engagement portion from the first position to the second position when the alignment pin assembly is moved from the pin retracted position towards the pin advanced position, and wherein the abutment member is releasably coupled to the base member of the alignment pin assembly when the deployment member is in the retracted position, and is fixedly secured to the base member of the alignment pin assembly when the deployment member is moved from the retracted position.

2. The surgical stapling instrument of claim 1, wherein the base member has an engagement portion, the engagement portion being engageable with the abutment member of the deployment member.

3. The surgical stapling instrument of claim 2, wherein the housing of the cartridge assembly defines a recess, and the engagement portion of the base member being aligned with the recess in the housing when the deployment member is in the retracted position.

4. The surgical stapling instrument of claim 3, wherein the engagement portion of the base member is out of alignment with the recess in the housing when the deployment member is moved from the retracted position.

5. The surgical stapling instrument of claim 3, wherein the engagement portion is configured to be cantilevered into the recess in the housing when the deployment member is in the retracted position.

6. The surgical stapling instrument of claim 5, wherein the engagement portion includes a snap feature configured to engage the abutment member of the deployment member to maintain engagement between the base member and the deployment member.

7. The surgical stapling instrument of claim 1, wherein the alignment pin assembly includes an alignment pin extending from the base member.

8. The surgical stapling instrument of claim 7, wherein the base member includes a pair of wings and the housing of the cartridge assembly defines a pair of slots, the wings being received within the slots to prevent rotation of the base member.

9. The surgical stapling instrument of claim 1, wherein the housing includes an alignment pin retaining portion defining a channel for receiving the alignment pin assembly.

10. A replaceable cartridge assembly comprising:
    a housing supporting a plurality of staples, the housing including a base portion and an alignment pin retaining portion, the alignment pin retaining portion including an inner surface defining a channel and a recess; and
    an alignment pin assembly slidably disposed within the channel and moveable between a retracted position and an advanced position, the alignment pin assembly including a base member and an alignment pin extending from the base member, the base member including an engagement portion that is movable from a first position located within the channel to a second position located within the recess to facilitate coupling of the engagement portion with a deployment member of a surgical stapling instrument, wherein the engagement portion is aligned with the recess when the alignment pin assembly is in the retracted position to permit the engagement portion to move from the first position to the second position, and wherein the inner surface of the alignment pin retaining portion prevents movement of the engagement portion from the first position to the second position when the alignment pin assembly is moved from the retracted position towards the advanced position.

11. The replaceable cartridge assembly of claim 10, wherein the engagement portion includes a snap feature, and the deployment member includes an abutment member, the snap feature being configured to maintain engagement between the base member and the deployment member.

12. The replaceable cartridge assembly of claim 10, wherein the base member includes a pair of wings and the housing defines a pair of slots, the wings being received within the slots to prevent rotation of the base member.

13. The replaceable cartridge assembly of claim 10, wherein the housing is configured to be releasably secured to an end effector of a surgical stapling instrument.

14. The replaceable cartridge assembly of claim 10, wherein the base member and the alignment pin are integrally formed.

15. The replaceable cartridge assembly of claim 10, wherein the engagement portion is out of alignment with the recess when the alignment pin assembly is moved from the retracted position.

16. The replaceable cartridge assembly of claim 15, wherein the housing is curved.

17. The replaceable cartridge assembly of claim 10, wherein the alignment pin includes a proximal portion having a first diameter and a distal portion having a second diameter, the first diameter being larger than the second diameter.

* * * * *